United States Patent
Wan et al.

(10) Patent No.: US 10,132,741 B2
(45) Date of Patent: Nov. 20, 2018

(54) INTEGRATED DEVICE FOR SAMPLING AND DETECTING FECAL SAMPLES

(71) Applicant: W.H.P.M. BIORESEARCH AND TECHNOLOGY CO., LTD., Beijing (CN)

(72) Inventors: John Wan, Beijing (CN); Qinghai Xia, Beijing (CN); Panpan Hou, Beijing (CN); Jie Liu, Beijing (CN)

(73) Assignee: W.H.P.M. BIORESEARCH AND TECHNOLOGY CO., LTD., Beijing (CN)

( * ) Notice: Subject to any disclaimer, the term of this patent is extended or adjusted under 35 U.S.C. 154(b) by 8 days.

(21) Appl. No.: 15/391,063

(22) Filed: Dec. 27, 2016

(65) Prior Publication Data

US 2018/0052096 A1   Feb. 22, 2018

(30) Foreign Application Priority Data

Aug. 19, 2016  (CN) .................... 2016 2 0912081 U

(51) Int. Cl.
*G01N 21/03*   (2006.01)
*G01N 33/483*  (2006.01)
(Continued)

(52) U.S. Cl.
CPC ......... *G01N 21/03* (2013.01); *A61B 10/0038* (2013.01); *B01L 3/5029* (2013.01);
(Continued)

(58) Field of Classification Search
CPC .... G01N 2001/0038; G01N 1/28; G01N 1/38; B01L 3/508; B01L 3/5082; B01L 3/50
(Continued)

(56) References Cited

U.S. PATENT DOCUMENTS

2004/0267159 A1* 12/2004 Yong .................... A61B 10/007
                                                         600/575
2005/0048670 A1*  3/2005 Wu ..................... A61B 10/0045
                                                         436/180
(Continued)

FOREIGN PATENT DOCUMENTS

CN    203241258     * 10/2013  ............... G01N 1/02
CN    203241258 U    10/2013
CN    104849440 A     8/2015

OTHER PUBLICATIONS

Extended European Search Report dated Sep. 12, 2017 issued in Application No. 16 205 282.3.

*Primary Examiner* — Michael P Lapage
(74) *Attorney, Agent, or Firm* — Scully Scott Murphy & Presser

(57) ABSTRACT

An integrated sampling and detecting device is provided. The device has a detector; a test strip holder, detachably provided in the detector; a collector, detachably contained in the detector; a faeces sample piece and a cushion block, for detachably sealing the collector; and a piercing part, provided on a bottom surface of the detector and configured to pierce the collector. The test strip holder and the collector are contained in the detector side by side. The collector is located between the test strip holder and the detector. A first outer side face of the collector is adjacent to an inner side wall of the detector. A second outer side face of the collector is adjacent to the test strip holder. A horizontal cross-section of the piercing part adapts to a bottom surface of the collector.

8 Claims, 15 Drawing Sheets

(51) Int. Cl.
*A61B 10/00* (2006.01)
*B01L 3/00* (2006.01)

(52) U.S. Cl.
CPC .... *G01N 33/4833* (2013.01); *B01L 2200/025* (2013.01); *B01L 2200/16* (2013.01); *B01L 2300/0672* (2013.01); *B01L 2300/0825* (2013.01); *B01L 2400/0683* (2013.01)

(58) Field of Classification Search
USPC .............................................. 356/244, 246
See application file for complete search history.

(56) References Cited

U.S. PATENT DOCUMENTS

| | | | | |
|---|---|---|---|---|
| 2009/0024055 A1* | 1/2009 | Nguyen | ............. | A61B 10/0038 600/562 |
| 2011/0130681 A1* | 6/2011 | Okumura | ........... | A61B 10/0038 600/573 |
| 2011/0177931 A1* | 7/2011 | Kelland | ............. | B01L 3/50215 494/36 |
| 2012/0264229 A1* | 10/2012 | Wan | .................. | A61B 10/0038 436/175 |

\* cited by examiner

INTEGRATED DEVICE FOR SAMPLING AND DETECTING FECAL SAMPLES

TECHNICAL FIELD

The invention relates to the technical field of medical detections, and in particular to an integrated sampling and detecting device.

BACKGROUND

At present, on a conventional faeces sampling and detecting device, a puncturing part is provided on a side, facing a collector, of a bottom surface of a container, so as to be capable of puncturing the collector during detection to make a diluent flow into the container.

The conventional puncturing part cannot completely puncture an aluminium foil at a bottom of the collector, such that the diluent cannot fully flow into the container, thereby influencing a detection effect and prolonging waiting time.

SUMMARY

The invention provides an integrated sampling and detecting device, which is intended to solve the problem of influence on a detection effect due to the fact that a diluent cannot fully flow into a container in the prior art.

The invention provides an integrated sampling and detecting device. The integrated sampling and detecting device comprises: a container; a test strip holder, detachably provided in the container; a collector, detachably contained in the container; a faeces sample piece and a cushion block, configured to detachably seal the collector; and a piercing part, provided on a bottom surface of the container and configured to pierce the collector, wherein the test strip holder and the collector are contained in the container side by side, the collector is located between the test strip holder and the container, a first outer side face of the collector is adjacent to an inner side wall of the container, a second outer side face of the collector is adjacent to the test strip holder, and a horizontal cross-section of the piercing part adapts to a bottom surface of the collector.

Furthermore, the piercing part is of a column structure, an end, configured to pierce the collector, of the column structure is provided with a pointed corner, a groove is provided on a side face of the column structure, and the groove extends from a top end of the column structure to a bottom end of the column structure.

Furthermore, spacing between two side walls of the groove is gradually increased to an outer side.

Furthermore, a bottom of the groove is an arc-shaped surface.

Furthermore, the first outer side face of the collector and the second outer side face of the collector are asymmetric structurally.

Furthermore, the first outer side face of the collector is a plane, and the second outer side face of the collector is a curved surface.

Furthermore, the integrated sampling and detecting device further comprises: a supporting platform provided at a bottom of the container and configured to support the collector.

Furthermore, a side face of the test strip holder is provided with a slope decreased from top to bottom, and an inner side of the container is provided with a convex rib adapting to the slope of the test strip holder.

Furthermore, a trench is provided on an outer side of the test strip holder, a test strip is mounted on the trench, an inner wall of one side, adjacent to the test strip, of the container is provided with a slope from top to bottom, three other inner walls of the container are provided with slopes from the top to a container critical line, a straight wall perpendicular to the bottom surface of the container is provided below the container critical line, and the container critical line is provided on the inner wall of the container and perpendicular to a length direction of the container.

Furthermore, a test strip holder critical line is provided on an inner side of the test strip holder, the inner side of the test strip holder is provided with a slope from a top to the test strip holder critical line, and a straight wall perpendicular to the bottom surface of the container is provided below the test strip holder critical line.

By means of the technical solutions of the invention, a horizontal cross-section of a piercing part is configured to adapt to a bottom surface of a collector, such that when the collector is assembled into a container, the piercing part pierces an aluminium foil at a bottom of the collector to make it enter the collector fully and exactly, thereby aiding in full and rapid outflow of a diluent with a faeces sample. By means of the configuration, the problem of influence on a detection effect due to the fact that a diluent cannot fully flow into a container in the prior art can be solved.

BRIEF DESCRIPTION OF THE DRAWINGS

The drawings of the description, forming a part of the application, are used to provide further understanding of the invention. The schematic embodiments and illustrations of the invention are used to explain the invention, and do not form improper limits to the invention. In the drawings.

Figure 1:
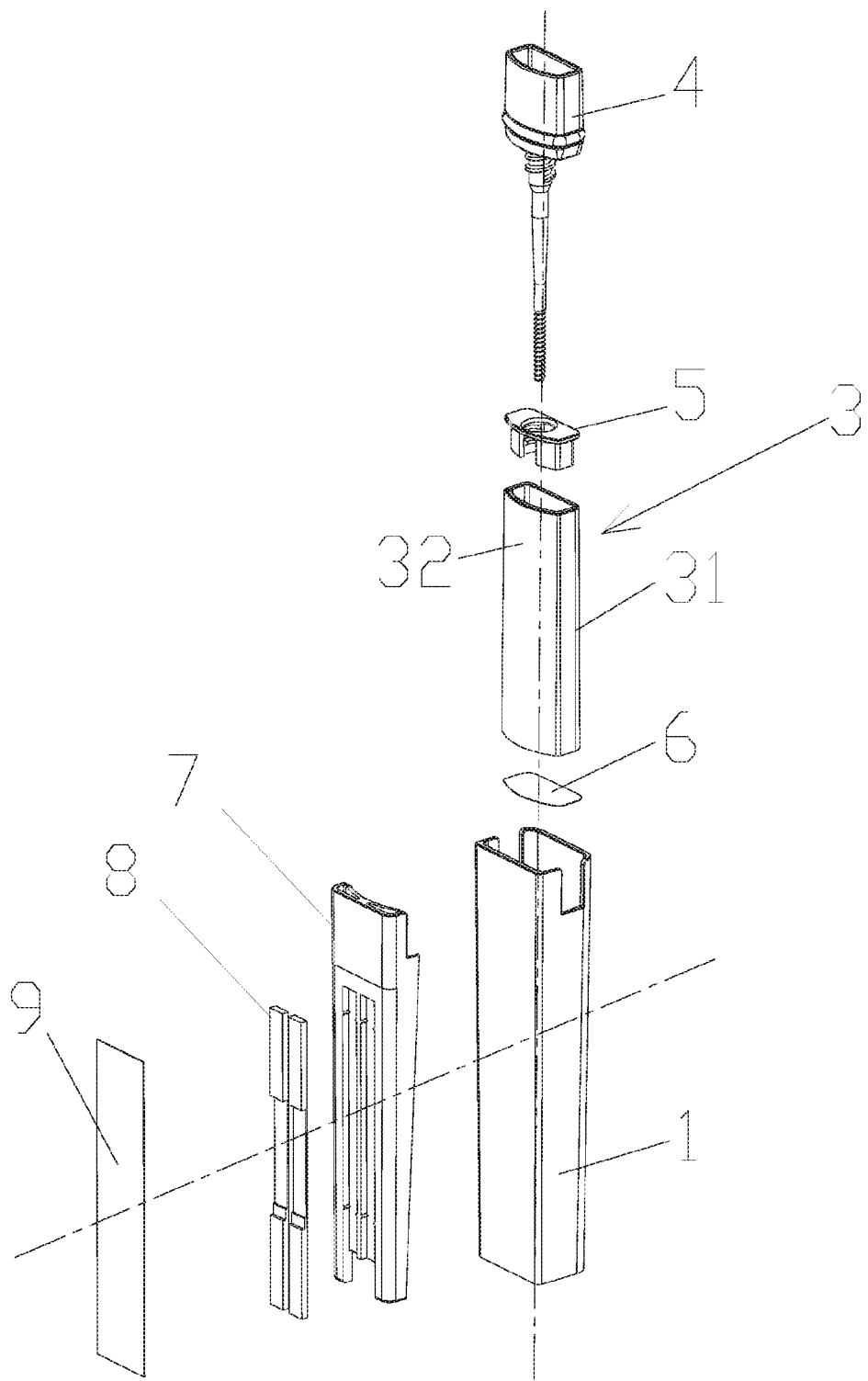
FIG. 1 is a three-dimensional breakdown structure diagram of an integrated sampling and detecting device according to an embodiment of the invention.
Figure 2:
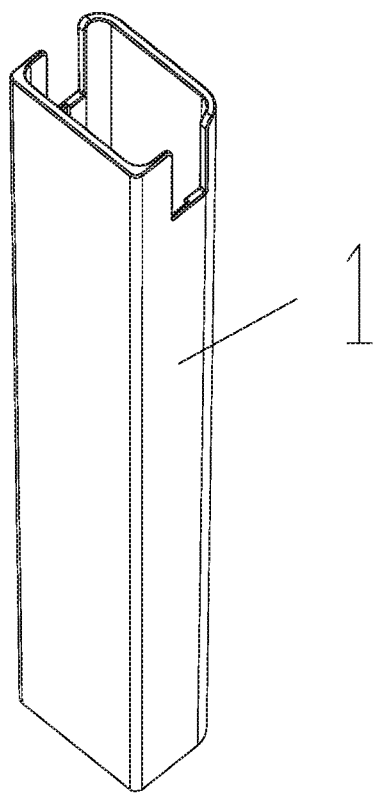
FIG. 2 is a three-dimensional structure diagram of a container of an integrated sampling and detecting device according to an embodiment of the invention.
Figure 3:
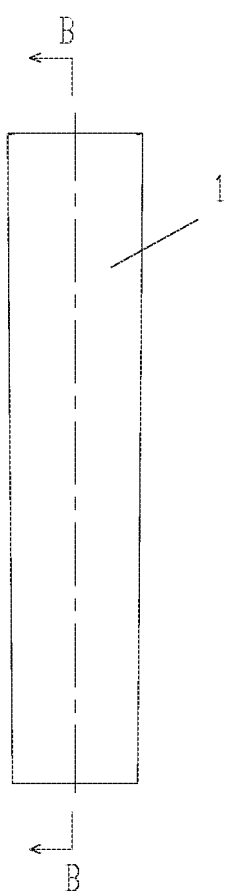
FIG. 3 is a front elevation view structure diagram of a container according to an embodiment of the invention.
Figure 4:
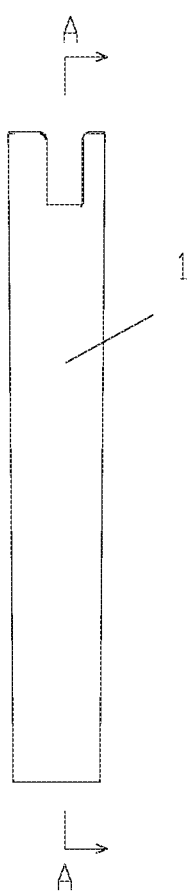
FIG. 4 is a side elevation view structure diagram of a container according to an embodiment of the invention.
Figure 5:
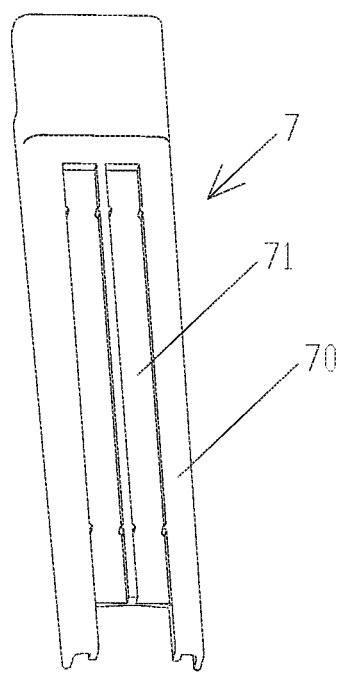
FIG. 5 shows a three-dimensional structure of a test strip holder according to an embodiment of the invention from a front elevation view direction.
Figure 6:
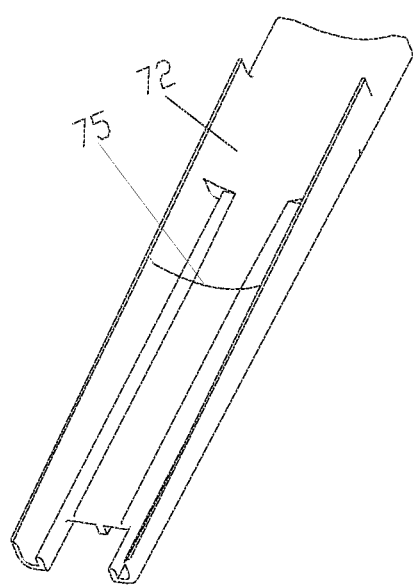
FIG. 6 shows a three-dimensional structure of a test strip holder according to an embodiment of the invention from a rear elevation view direction.
Figure 7:
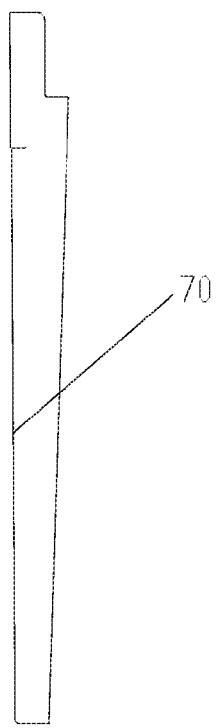
FIG. 7 is a side elevation view structure diagram of a test strip holder according to an embodiment of the invention.
Figure 8:
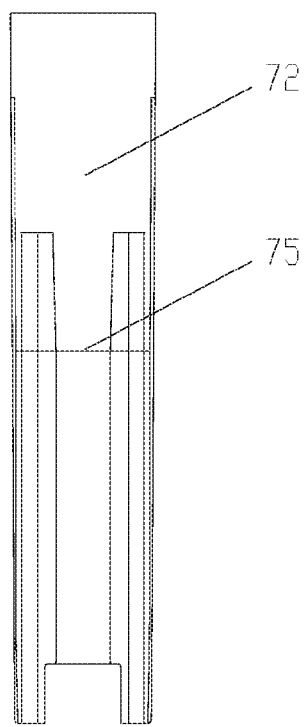
FIG. 8 is a rear elevation view plane structure diagram of a test strip holder according to an embodiment of the invention.
Figure 9:
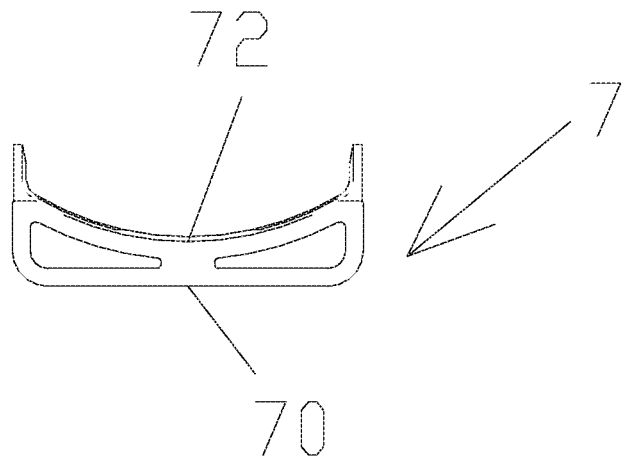
FIG. 9 is a top plan view structure diagram of a test strip holder according to an embodiment of the invention.

Wherein, the drawings include the following drawing mark illustrations:

1, container; 3, collector; 4, faeces sample piece; 5, cushion block; 6, aluminium foil; 7, test strip holder; 8, test strip; 9, transparent label; 13, pointed corner; 14, piercing part; 142, groove; 31, first outer side face; 32, second outer side face; 10, bottom surface; 11, supporting platform; 111, convex rib; 113, container critical line; 70, outer side of test strip holder; 71, trench; 72, inner wall; and 75, test strip holder critical line.

DETAILED DESCRIPTION OF THE EMBODIMENTS

The technical solutions in the embodiments of the invention will be clearly and completely described below in conjunction with the drawings in the embodiments of the invention. Apparently, the described embodiments are only a part of embodiments of the invention, not all of the embodiments. The following descriptions for at least one exemplar embodiment are only illustrative, and will not definitely serve as any limits to application or usage of the invention. Based on the embodiments of the invention, all of other embodiments, obtained by those skilled in the art without making creative works, fall within the protective scope of the invention.

It is important to note that terms used herein only aim to describe specific implementations, and are not intended to limit exemplar implementations of the application. For instance, unless otherwise directed by the context, singular forms of terms used herein are intended to include plural forms. Besides, it will be also appreciated that when terms 'contain' and/or 'include' are used in the description, it is pointed out that features, steps, operations, devices, assemblies and/or a combination thereof exist.

Unless otherwise specified, relative arrangements of components and steps elaborated in these embodiments, numeric expressions and numeric values do not limit the scope of the invention. Meanwhile, it shall be understood that in order to facilitate descriptions, the size of each part shown in the drawings is not drawn in accordance with an actual proportional relation. Technologies, methods and devices known by those skilled in the related art may not be discussed in detail. However, where appropriate, the technologies, the methods and the devices shall be regarded as part of the authorized description. In all examples shown and discussed herein, any specific values shall be interpreted as only exemplar values instead of limited values. As a result, other examples of the exemplar embodiments may have different values. It shall be noted that similar marks and letters represent similar items in the following drawings. As a result, once a certain item is defined in one drawing, it is unnecessary to further discus the certain item in the subsequent drawings.

In the descriptions of the invention, it is necessary to understand that orientation or position relations indicated by localizers such as 'front, back, up, down, left and right', 'transverse, vertical, perpendicular and horizontal' and 'top and down' are usually based on orientation or position relations shown in the drawings and are only intended to describe the invention and simplify the descriptions. Without making contrary illustrations, these localizers do not indicate and imply that devices or elements must have specific orientations or are constructed and operated in specific orientations. Thus, they cannot be understood as limits to the protective scope of the invention. Localizers 'inside and outside' refer to inside and outside an own profile of each component.

In order to facilitate descriptions, spatial relative terms such as 'over', 'above', 'on an upper surface' and 'upper' can be used herein, and are used to describe a spatial position relation between a device or feature and other devices or features shown in the drawings. It will be appreciated that the spatial relative terms aim to contain different orientations in usage or operation besides the orientations of the devices described in the drawings. For instance, if the devices in the drawings are inverted, devices described as 'above other devices or structures' or 'over other devices or structures' will be located as 'below other devices or structures' or 'under other devices or structures'. Thus, an exemplar term 'above' may include two orientations namely 'above' and 'below'. The device may be located in other different modes (rotated by 90 degrees or located in other orientations), and spatial relative descriptions used herein are correspondingly explained.

In addition, it is important to note that terms 'first', 'second' and the like are used to limit parts, and are only intended to distinguish corresponding parts. If there are no otherwise statements, the above terms do not have special meanings, such that they cannot be understood as limits to the protective scope of the invention.

As shown in FIG. 1 to FIG. 16, the embodiments of the invention provide an integrated sampling and detecting device. The integrated sampling and detecting device comprises: a container 1; a test strip holder 7, detachably provided in the container 1; a collector 3, detachably contained in the container 1; a faeces sample piece 4 and a cushion block 5, configured to detachably seal the collector 3; and a piercing part 14, provided on a bottom surface 10 of the container 1 and configured to pierce the collector 3, wherein the test strip holder 7 and the collector 3 are contained in the container 1 side by side, the collector 3 is located between the test strip holder 7 and the container 1, a first outer side face 31 of the collector 3 is adjacent to an inner side wall of the container 1, a second outer side face 32 of the collector 3 is adjacent to the test strip holder 7, and a horizontal cross-section of the piercing part 14 adapts to a bottom surface 10 of the collector 3.

By means of the configuration mode, a horizontal cross-section of the piercing part 14 is configured to adapt to the bottom surface 10 of the collector 3, such that when the collector 3 is assembled into the container 1, the piercing part 14 pierces an aluminium foil at the bottom of the collector 3 to make it enter the collector 3 fully and exactly, thereby aiding in full and rapid outflow of a diluent with a faeces sample. In addition, because the test strip holder 7 and the collector 3 are sealed in the container 1, a detection sample and a solution in the collector 3 will not flow out of the container 1, such that after the detection sample is detected, it is unnecessary to perform processing, and secondary pollution of medical wastes is avoided.

In the invention, in order to make a diluent with a faeces sample capable of rapidly flowing out, as shown in FIG. 17 to FIG. 20, the piercing part 14 is of a column structure, an end, configured to pierce the collector 3, of the column structure is provided with a pointed corner 13, a groove 142 is provided on a side face of the column structure, and the groove 142 extends from a top end of the column structure to a bottom end of the column structure.

By means of the configuration mode, when the aluminium foil 6 at the bottom of the collector 3 is pierced, the end, configured to pierce the collector 3, of the column structure is provided with the pointed corner 13, such that the aluminium foil 6 can be rapidly pierced by means of the pointed corner 13. In addition, the groove 142 is provided on the side face of the column structure and the groove 142 extends from the top end of the column structure to the bottom end of the column structure, such that when the pointed corner 13 pierces the aluminium foil 6, a diluent with a faeces sample can rapidly flow out along the groove 142 extending from the top end of the column structure to the bottom end of the column structure.

Specifically, in order to further make the diluent with the faeces sample rapidly flow out, spacing between two side walls of the groove 142 of the piercing part 14 can be set to be gradually increased to an outer side. The bottom of the groove 142 is an arc-shaped surface. By means of the configuration mode, the diluent can rapidly flow out.

In the invention, in order to avoid a phenomenon of mis-bonding of a bar code, the first outer side face 31 of the collector 3 and the second outer side face 32 of the collector 3 can be set to be asymmetric structurally.

Specifically, as shown in FIG. 1 to FIG. 5, in the invention, the first outer side face 31 of the collector 3 is adjacent to an inner side wall of the container 1, the second outer side face 32 of the collector is adjacent to the test strip holder 7, and the first outer side face 31 and second outer side face 32 of the collector are asymmetric structurally. Thus, two side faces of the collector can be obviously distinguished, and a side face bonded with a bar code and a side face facing a container or attached to the container can be judged. So, the problem that a side, bonded with a bar code, of a collector is mis-assembled into a side, close to a test strip holder, of a container is solved. In addition, the first outer side face 31 of the collector can be bonded with a text label of a bar code, thereby avoiding mis-bonding of the bar code. A recess area may be provided on the second outer side face 32, not bonded with a bar code, of the collector 3, and the recess area is provided with a convex rib or a convex needle-shaped body or a convex column body of the collector, such that it is very difficult to bond the second outer side face 32, not bonded with a bar code, with a bar code, thereby avoiding the phenomenon of mis-bonding of a bar code.

In addition, once a side bonded with a bar code is mis-assembled into a side, close to a test strip holder, of a container in the prior art, it is difficult to take out and reassemble the mis-assembled part due to the fact that the whole faeces sampling and detecting device has a compact structure, thereby scraping a set of faeces sampling and detecting device. Moreover, even if the collector can be taken out, the bar code thereon is probably abraded in assembly and disassembly processes, and reading of the bar code will be influenced. The above problem can be avoided by means of the structure of the collector in the invention.

Figure 10:
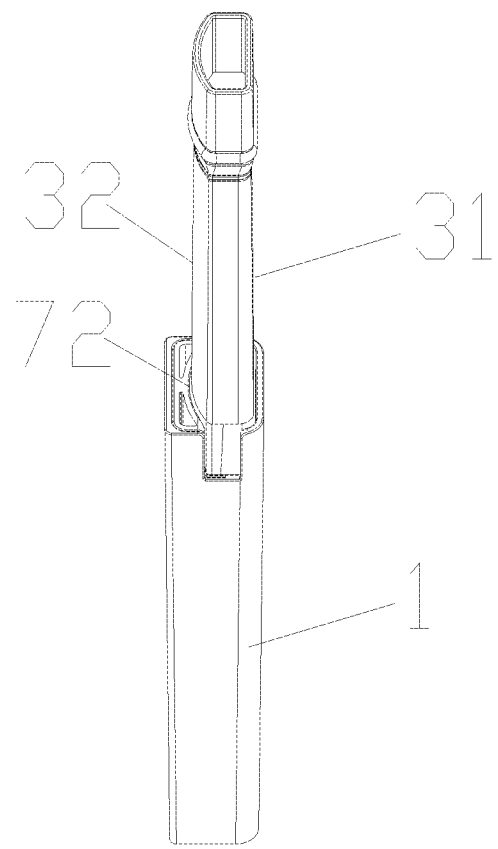
FIG. 10 is a mounting diagram of a faeces sample piece, a cushion block, a collector and a test strip holder according to an embodiment of the invention, wherein the faeces sample piece, the cushion block, the collector and the test strip holder are assembled into a container in a forward direction.

According to an embodiment of the invention, during the manufacture of the collector 3, the mold for forming the collector 3 is withdrawn inwardly from the bottom to the top of the collector 3, and accordingly, a lower end of the collector 3 is larger than an upper end of the collector while a lower end of the container 1 is smaller than an upper end of the container 1. In conjunction with an circular arc shape of the test strip holder 7, as shown in FIG. 10, the faeces sample piece 4, the cushion block 5, the collector 3, the test strip holder 7 and the container 1 are smoothly assembled without interference. In addition, due to threaded fit between the faeces sample piece 4 and the cushion block 5, the directions of arc surfaces of the faeces sample piece 4 and the cushion block 5 must be consistent with the direction of an arc surface of the collector 3. That is, the combination of the faeces sample piece 4, the cushion block 5 and the collector 3 has forward and reverse properties, so the faeces sample piece 4, the cushion block 5 and the collector 3 can be smoothly assembled into the container 1. The second outer side face 32 of the collector 3 is in a convex circular arc shape, the first outer side face 31 is a plane, an inner wall 72 of the test strip holder is in a recessed circular arc shape for instance, and the circular arc-shaped second outer side face 32 matches with the inner wall 72 of the test strip holder. Thus, as shown in FIG. 10, the collector 3, the test strip holder 7 and the container 1 can be smoothly assembled during forward mounting.

Figure 11:
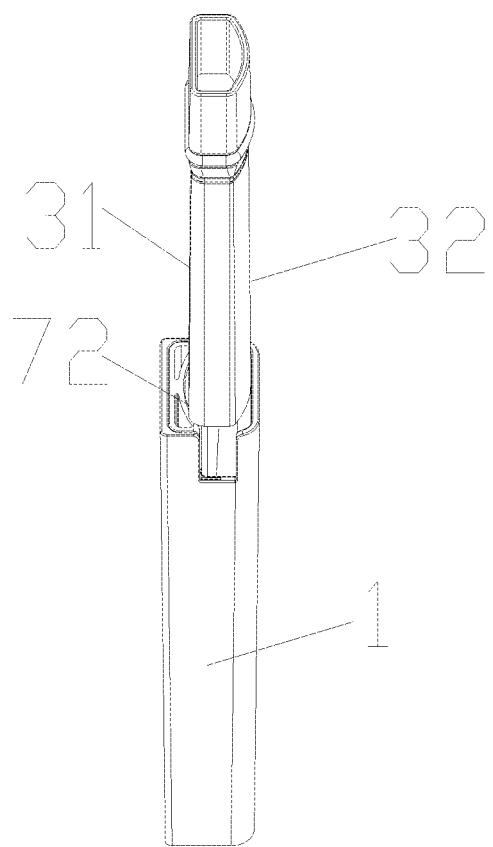
FIG. 11 is a mounting diagram of a faeces sample piece, a cushion block, a collector and a test strip holder according to an embodiment of the invention, wherein the faeces sample piece, the cushion block, the collector and the test strip holder are assembled into a container in a reverse direction.
Figure 12:
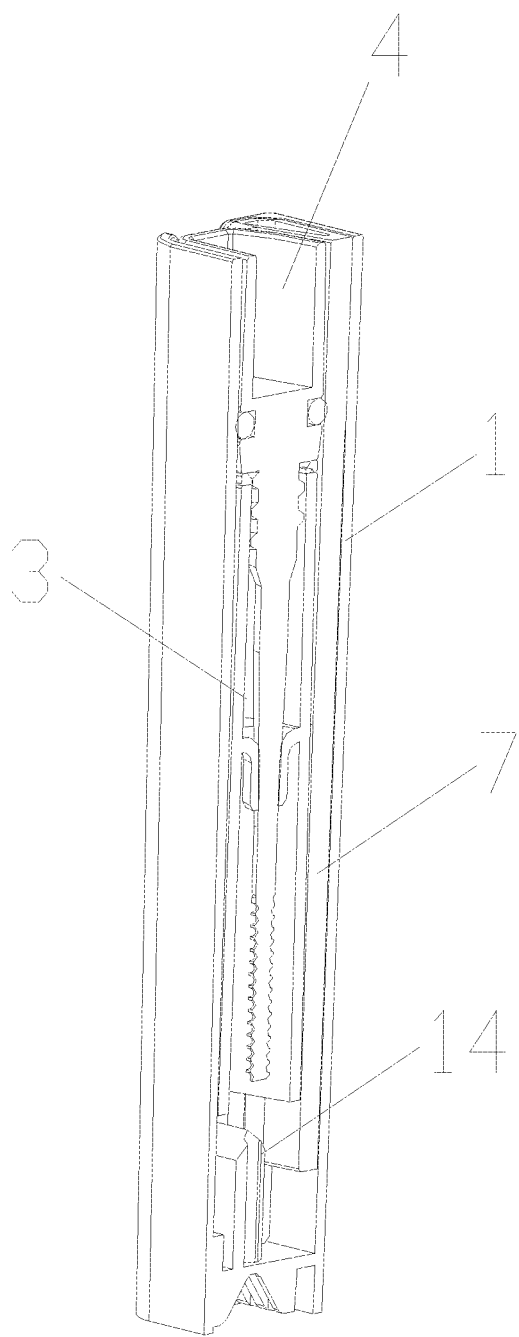
FIG. 12 is a three-dimensional structure diagram showing assembly of a faeces sample piece, a cushion block, a collector and a test strip holder into a container according to an embodiment of the invention.
Figure 13:
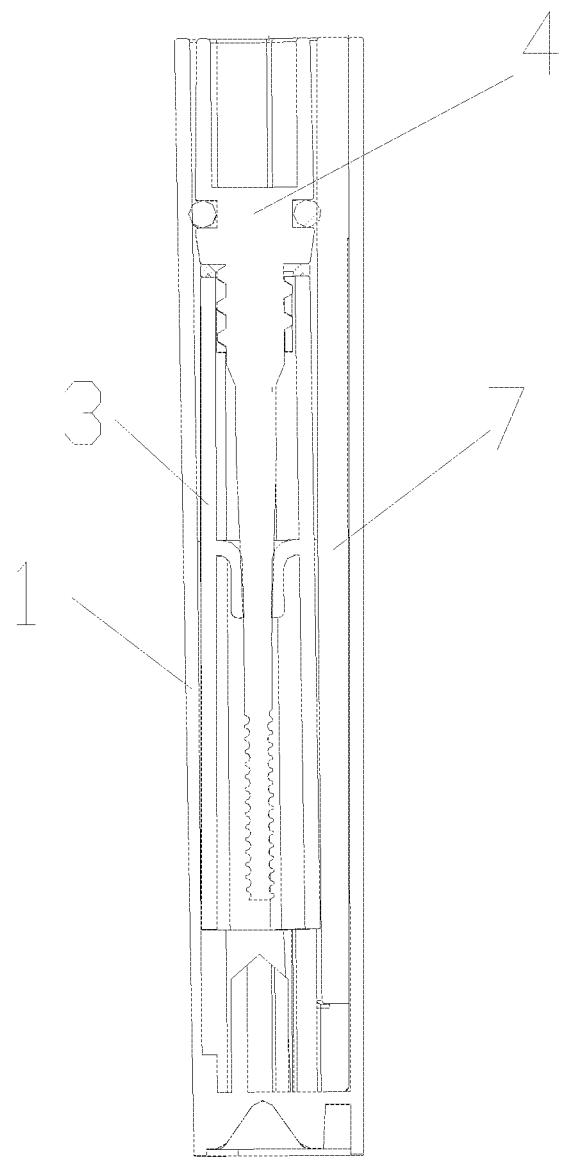
FIG. 13 is a section view diagram showing assembly of a faeces sample piece, a cushion block, a collector and a test strip holder into a container according to an embodiment of the invention.

As shown in FIG. 11, if the components are mounted reversely, that is, if the first outer side face 31 matches with or is attached to the circular arc-shaped inner wall 72 of the test strip holder and the circular arc-shaped second outer side face 32 matches with or is attached to the inclined or straight inner wall of the container 1, a situation that a fitting surface between a plane and an arc-shaped surface does not fit will be caused, and the faeces sample piece 4, the cushion block 5, the collector 3, the test strip holder 7 and the container 1 are stuck due to interference. That is, during reverse mounting, the faeces sample piece 4, the cushion block 5, the collector 3 and the test strip holder 7 cannot be mounted into the container 1. Thus, a mis-assembly prevention effect can be achieved at the beginning of mounting.

In addition, as shown in FIG. 1, the integrated sampling and detecting device with a mis-assembly prevention structure may further comprise: the cushion block 5 in threaded connection with the faeces sample piece 4, the aluminium foil 6 packaged at the bottom of the collector 3, a test strip 8 mounted on the test strip holder, and a transparent label 9 covering the test strip 8. Other structures of the integrated sampling and detecting device with a mis-assembly prevention structure or relevant functions and structures not mentioned by the above parts may adopt a relevant technology in CN201320139144.6 or refer to descriptions in CN201320139144.6.

Specifically, in the invention, in view of the problem of convenient manufacturing, the first outer side face 31 of the collector 3 can be a plane, and the second outer side face 32 of the collector 3 can be a curved surface. By means of the configuration mode, the first outer side face 31 of the collector 3 is configured as a plane for conveniently bonding a bar code, and the second outer side face 32 of the collector 3 is configured as a curved surface for preventing or hindering bonding of the bar code and fitting the test strip holder.

Furthermore, in order to facilitate outflow of the diluent with the faeces sample, the integrated sampling and detecting device may be further configured to comprise: a supporting platform 11 provided at the bottom of the container 1 and configured to support the collector 3. By means of the configuration mode, the supporting platform 11 is provided on the bottom surface 10 of the container and protrudes from the bottom surface 10 of the container so as to ensure a certain distance between the bottom of the collector 3 and the bottom surface of the container 1, thereby facilitating outflow of the diluent with the faeces sample.

In the invention, in order to ensure that a fit part of the test strip holder 7 and the container 1 can be self-sealed, the side face of the test strip holder 7 can be configured to be provided with a slope decreased from top to bottom, and the inner side of the container 1 is provided with a convex rib 111 adapting to the slope of the test strip holder 7.

By means of the configuration mode, the convex rib 111 on the inner side of the container 1 fits the slope of the test strip holder, such that the test strip holder 7 can be assembled into the container 1 and clinged to the container 1 at the same time when the test strip holder 7 is assembled into the container, thereby making the fit part of the test strip holder 7 and the container 1 self-sealed.

Figure 15:
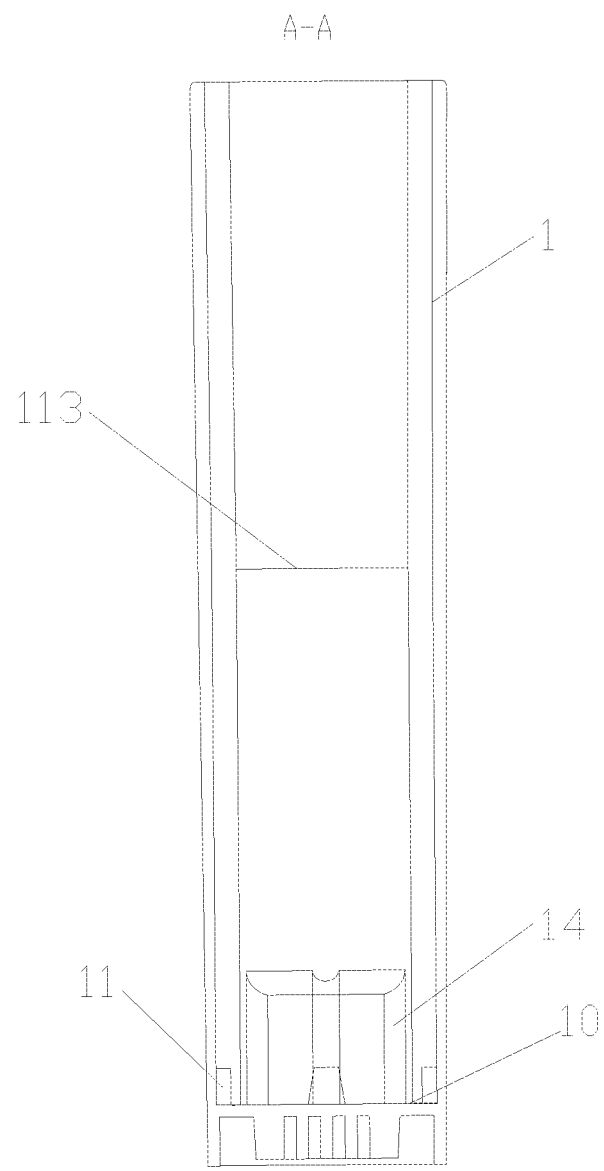
FIG. 15 is an A-A section view structure diagram of FIG. 4.
Figure 16:
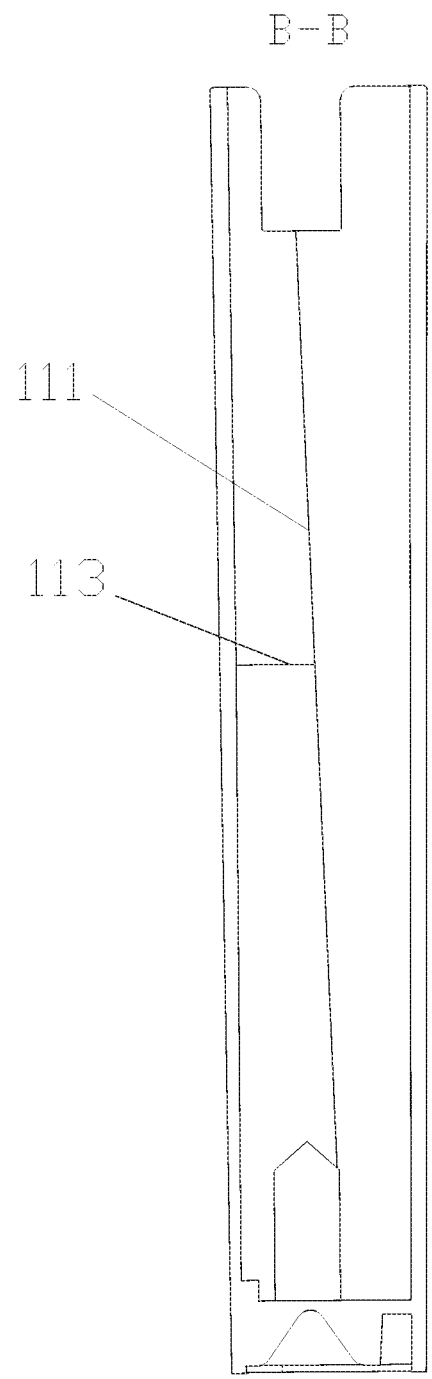
FIG. 16 is a B-B section view structure diagram of FIG. 3.
Figure 17:
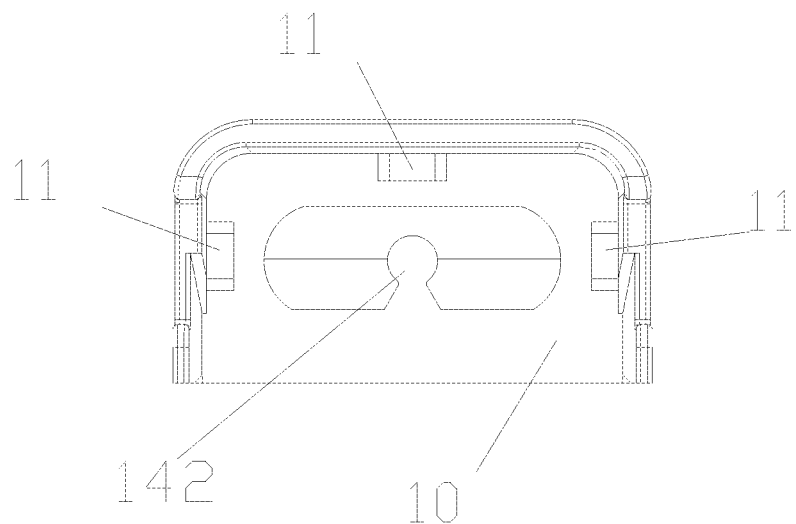
FIG. 17 is a top plan view structure diagram showing mounting of a piercing part in a container according to an embodiment of the invention.
Figure 18:
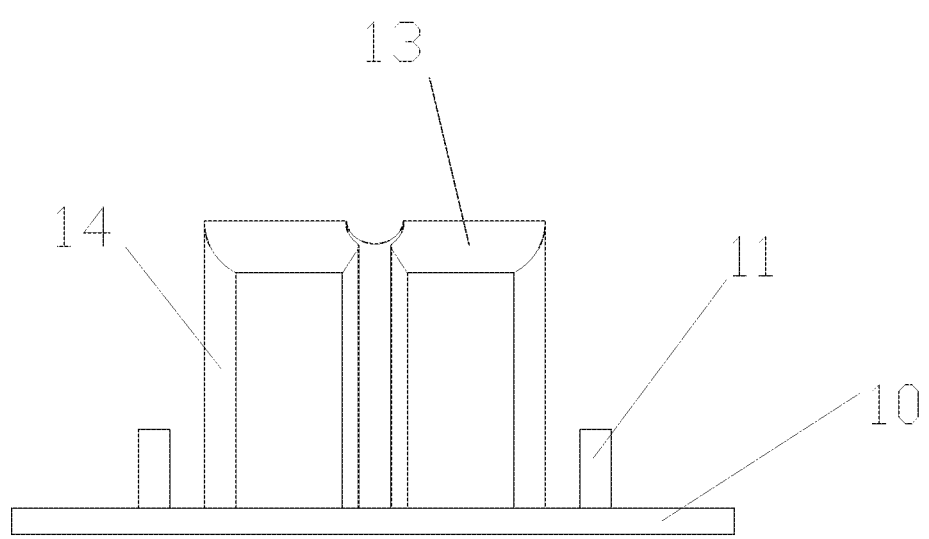
FIG. 18 is a front elevation view structure diagram of a piercing part according to an embodiment of the invention.
Figure 19:
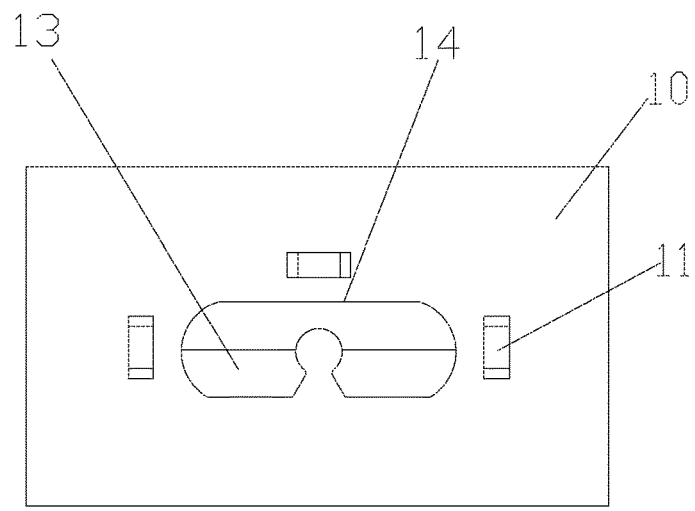
FIG. 19 is a top plan view structure diagram of a piercing part according to an embodiment of the invention.
Figure 20:
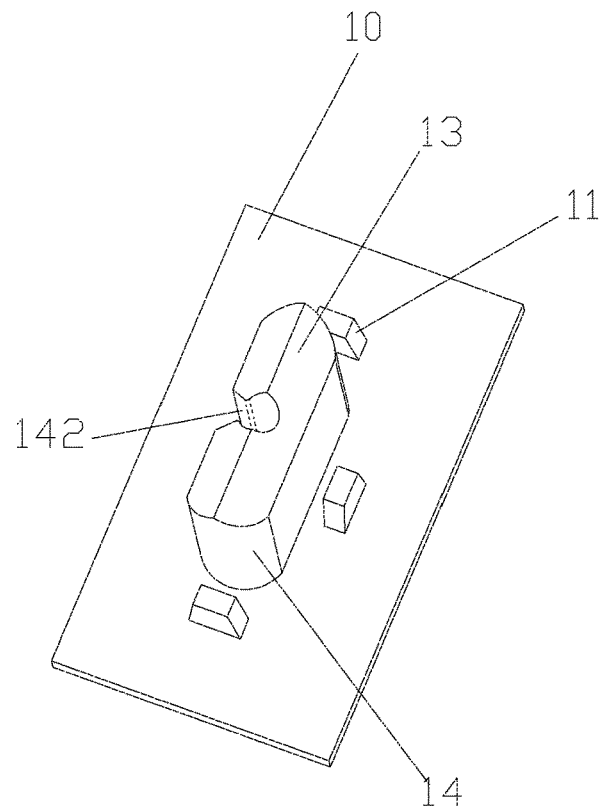
FIG. 20 is a three-dimensional structure diagram of a piercing part according to an embodiment of the invention.

Furthermore, in order to press the collector 3 in place, as shown in FIG. 15 to FIG. 16, a trench 71 is provided on an outer side 70 of the test strip holder, a test strip 8 is mounted on the trench 71, an inner wall of one side, adjacent to the test strip 8, of the container 1 is provided with a slope from top to bottom, three other inner walls of the container 1 are provided with slopes from the top to a container critical line 113, a straight wall perpendicular to the bottom surface 10 of the container 1 is provided below the container critical line 113, and the container critical line 113 is provided on the inner wall of the container 1 and perpendicular to a length direction of the container 1.

Specifically, in the invention, the container critical line is provided on the side of the collector of the container, starts from a convex rib on one side of the container and terminates to a convex rib on the other side of the container. The container critical line is located at a position, ⅓ to ½ of a height of the whole container, below a top opening.

Figure 14:
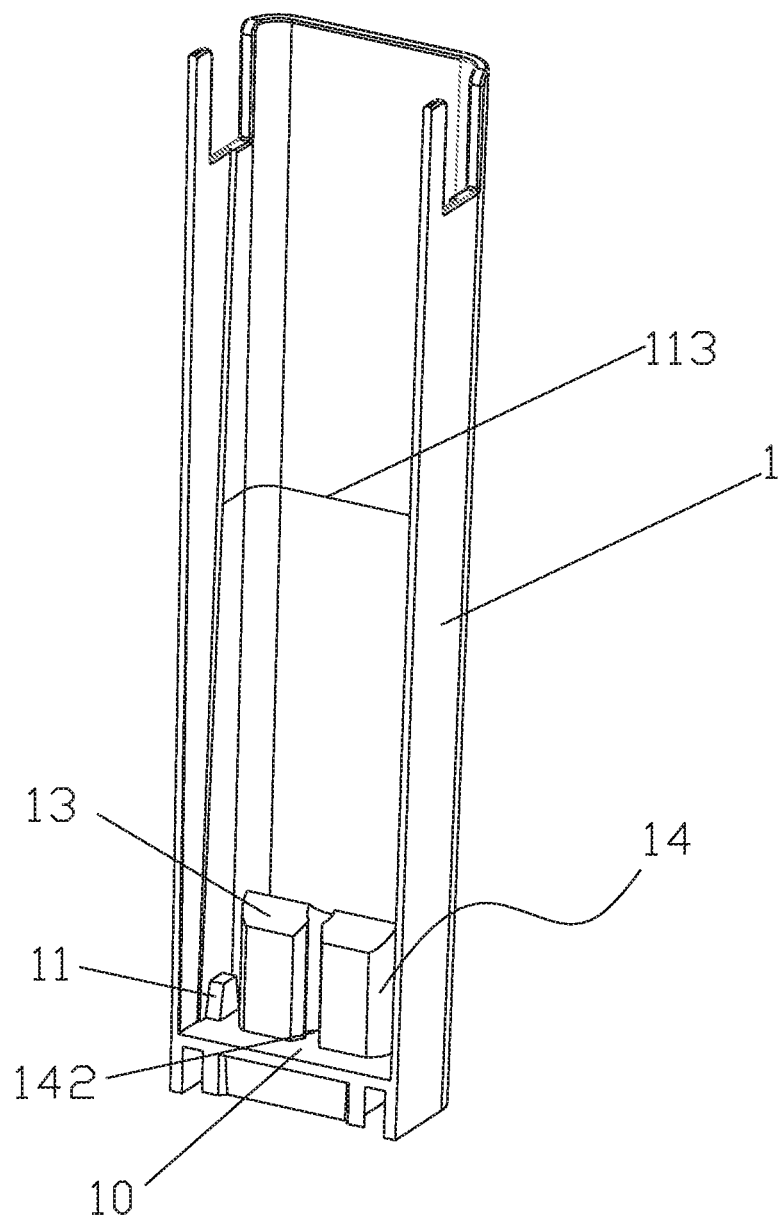
FIG. 14 is a structural diagram showing mounting of a piercing part in a container according to an embodiment of the invention.

As shown in FIG. 14, in the invention, a test strip holder critical line 75 is provided on an inner side of the test strip holder 7, the inner side of the test strip holder 7 is provided with a slope from a top to the test strip holder critical line 75, and a straight wall perpendicular to the bottom surface 10 of the container 1 is provided below the test strip holder critical line 75.

By means of the configuration mode, the test strip holder critical line 75 is perpendicular to the length direction of the test strip holder 7 and matches with the critical line of the container 1. The test strip holder critical line is located, for instance, at a position, ⅓ to ½ of a height of the whole test strip holder, from a top end of the test strip holder. The straight wall structures are provided below the critical lines of the test strip holder 7 and the container 1, so as to press the collector 3 in place conveniently.

The integrated sampling and detecting device of the invention is improved on the basis of a piercing part of a prior faeces sampling and detecting device. A horizontal cross-section of a piercing part is configured to adapt to a bottom surface of a collector, thereby aiding in full and rapid outflow of a diluent with a faeces sample. In addition, because a test strip holder and the collector are sealed in a container, so a detection sample and a solution in the collector will not flow out of the container, such that after the detection sample is detected, it is unnecessary to perform processing, and secondary pollution of medical wastes is avoided.

The above is only the preferred embodiments of the invention, and is not used to limit the invention. There can be various modifications and variations in the invention for those skilled in the art. Any modifications, equivalent replacements, improvements and the like within the spirit and principle of the invention shall fall within the protective scope of the invention.

The invention claimed is:

1. An integrated sampling and detecting device, comprising:
   a container;
   a test strip holder, detachably provided in the container;
   a collector, detachably contained in the container;
   a faeces sample piece and a cushion block, configured to detachably seal the collector; and
   a piercing part, provided on a bottom surface of the container and configured to pierce the collector,
   wherein the test strip holder and the collector are contained in the container side by side, the collector is located between the test strip holder and the container, a first outer side face of the collector is adjacent to an inner side wall of the container, a second outer side face of the collector is adjacent to the test strip holder, and a horizontal cross-section of the piercing part adapts to a bottom surface of the collector,
   wherein the piercing part is of a column structure configured to pierce the collector, an end of the column structure is provided with a pointed corner, a groove is provided on a side face of the column structure, and the groove extends from a top end of the column structure to a bottom end of the column structure, and
   wherein spacing between two side walls of the groove gradually increases from the intersection of the two side walls of the groove outwardly towards an exterior surface of the piercing part.

2. The integrated sampling and detecting device according to claim 1, wherein the groove is arc-shaped as the groove extends along the piercing part.

3. The integrated sampling and detecting device according to claim 1, wherein the first outer side face of the collector and the second outer side face of the collector are asymmetric structurally.

4. The integrated sampling and detecting device according to claim 3, wherein the first outer side face of the collector is a plane, and the second outer side face of the collector is a curved surface.

5. The integrated sampling and detecting device according to claim 1, further comprising:
   a supporting platform provided at a bottom of the container and configured to support the collector.

6. The integrated sampling and detecting device according to claim 1, wherein a side face of the test strip holder is provided with a slope decreased from top to bottom, and an inner side of the container is provided with a convex rib adapting to the slope of the test strip holder.

7. The integrated sampling and detecting device according to claim 6, wherein a trench is provided on an outer side of the test strip holder, a test strip is mounted on the trench, an inner wall of one side, adjacent to the test strip, of the container is provided with a slope from top to bottom, three other inner walls of the container are provided with slopes from the top to a container critical line, a straight wall perpendicular to the bottom surface of the container is provided below the container critical line, and the container critical line is provided on the inner wall of the container and perpendicular to a length direction of the container.

8. The integrated sampling and detecting device according to claim 7, wherein a test strip holder critical line is provided on an inner side of the test strip holder, the inner side of the test strip holder is provided with a slope from a top to the test strip holder critical line, and a straight wall perpendicular to the bottom surface of the container is provided below the test strip holder critical line.

* * * * *